United States Patent
Tegels

(10) Patent No.: US 8,540,750 B2
(45) Date of Patent: Sep. 24, 2013

(54) DUAL LUMEN BOND FOR VASCULAR CLOSURE DEVICE AND METHODS

(75) Inventor: Zachary J. Tegels, Minneapolis, MN (US)

(73) Assignee: St. Jude Medical Puerto Rico LLC, Caguas, PR (US)

( * ) Notice: Subject to any disclaimer, the term of this patent is extended or adjusted under 35 U.S.C. 154(b) by 0 days.

(21) Appl. No.: 13/425,314

(22) Filed: Mar. 20, 2012

(65) Prior Publication Data

US 2012/0245517 A1    Sep. 27, 2012

Related U.S. Application Data

(60) Provisional application No. 61/466,867, filed on Mar. 23, 2011.

(51) Int. Cl.
*A61B 17/03* (2006.01)
*A61M 25/00* (2006.01)

(52) U.S. Cl.
USPC ........................................ 606/213; 604/96.01

(58) Field of Classification Search
USPC ...................................... 604/96.01; 606/213
See application file for complete search history.

(56) References Cited

U.S. PATENT DOCUMENTS

| | | | | | |
|---|---|---|---|---|---|
| 5,486,195 | A | * | 1/1996 | Myers et al. | 606/213 |
| 5,725,551 | A | * | 3/1998 | Myers et al. | 606/213 |
| 5,810,849 | A | * | 9/1998 | Kontos | 606/144 |
| 2003/0125766 | A1 | * | 7/2003 | Ding | 606/213 |
| 2005/0113798 | A1 | * | 5/2005 | Slater et al. | 604/508 |
| 2005/0234474 | A1 | * | 10/2005 | DeMello et al. | 606/113 |
| 2006/0149218 | A1 | * | 7/2006 | Slater et al. | 604/509 |
| 2010/0030192 | A1 | * | 2/2010 | Gunderson et al. | 604/524 |

* cited by examiner

*Primary Examiner* — Aarti B Berdichevsky
(74) *Attorney, Agent, or Firm* — Holland & Hart

(57) ABSTRACT

A vascular closure device that includes an inflation tube, a flashback tube, a dual lumen tube, a bond portion, and an inflatable balloon. The inflation tube defines an inflation lumen. The flashback tube defines a flashback lumen. The dual lumen tube has first and second lumens and is positioned distal of the inflation tube and flashback tube. The inflation tube and flashback tube are integrally connected to the dual lumen tube at the bond portion with the inflation lumen in fluid communication with the first lumen and the flashback lumen in fluid communication with the second lumen. The inflatable balloon is mounted at a distal end of the dual lumen tube and is in fluid communication with the inflation lumen.

21 Claims, 11 Drawing Sheets

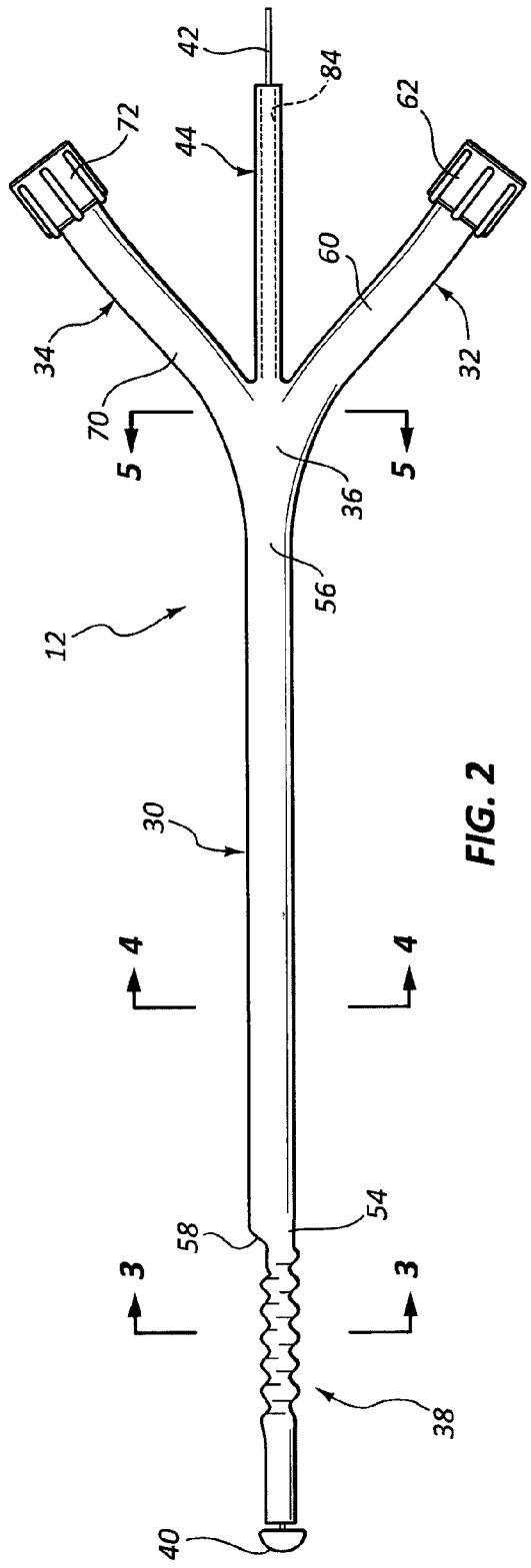
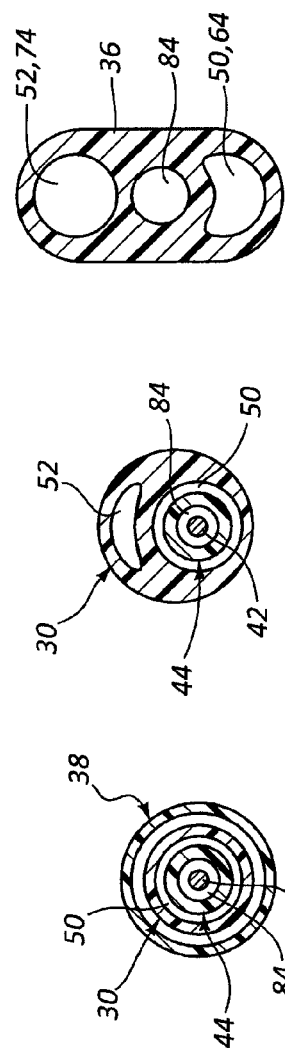

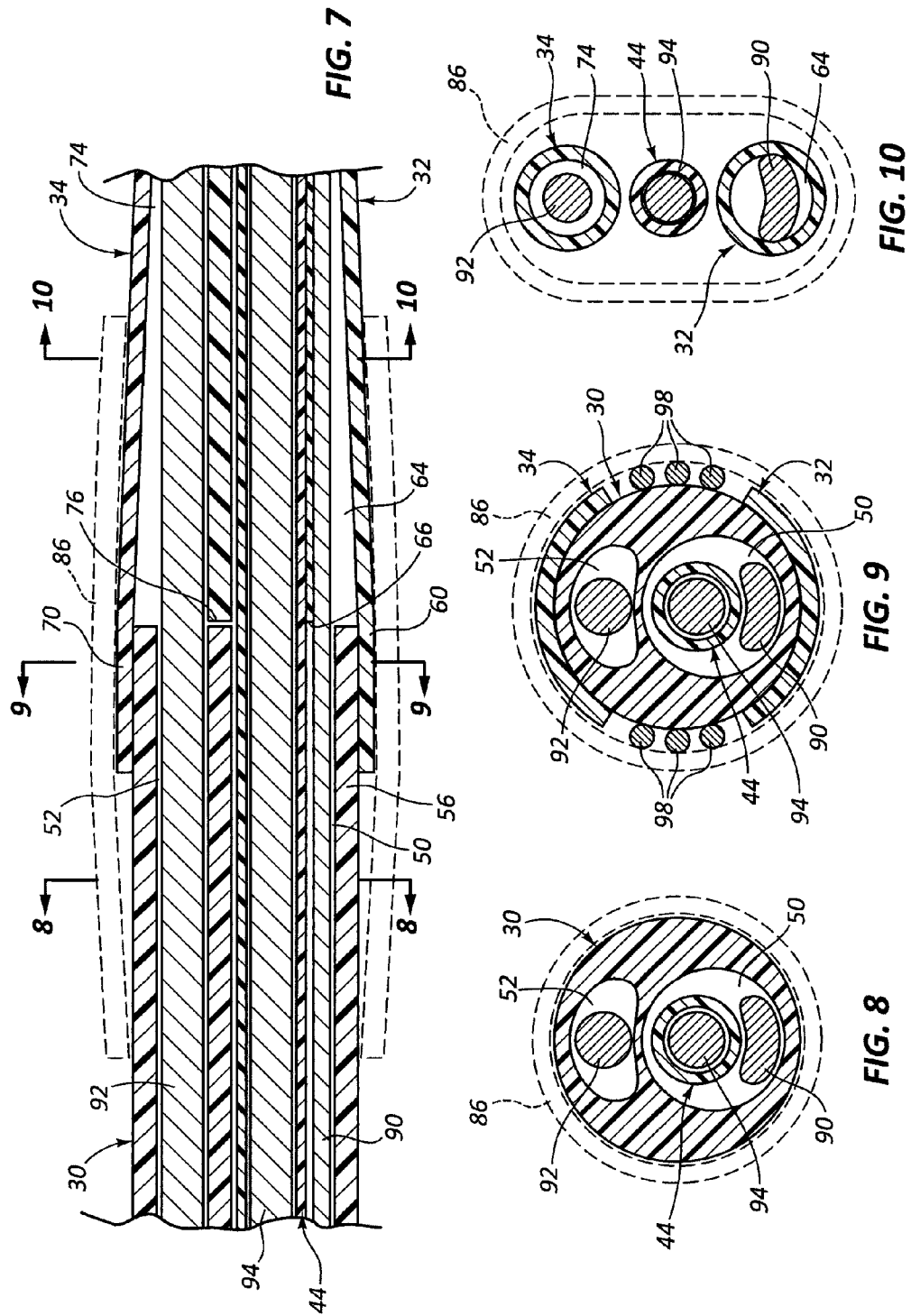

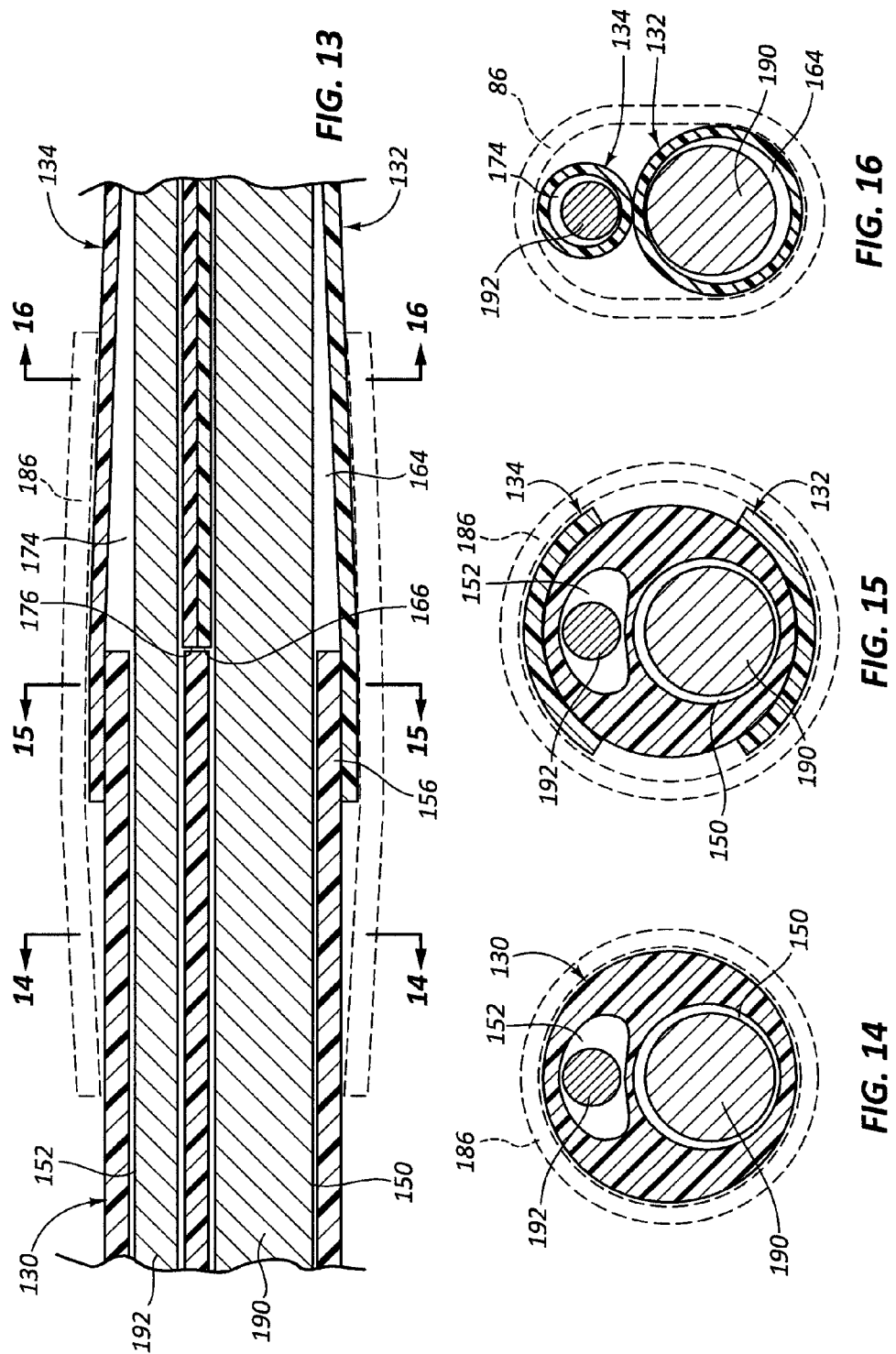

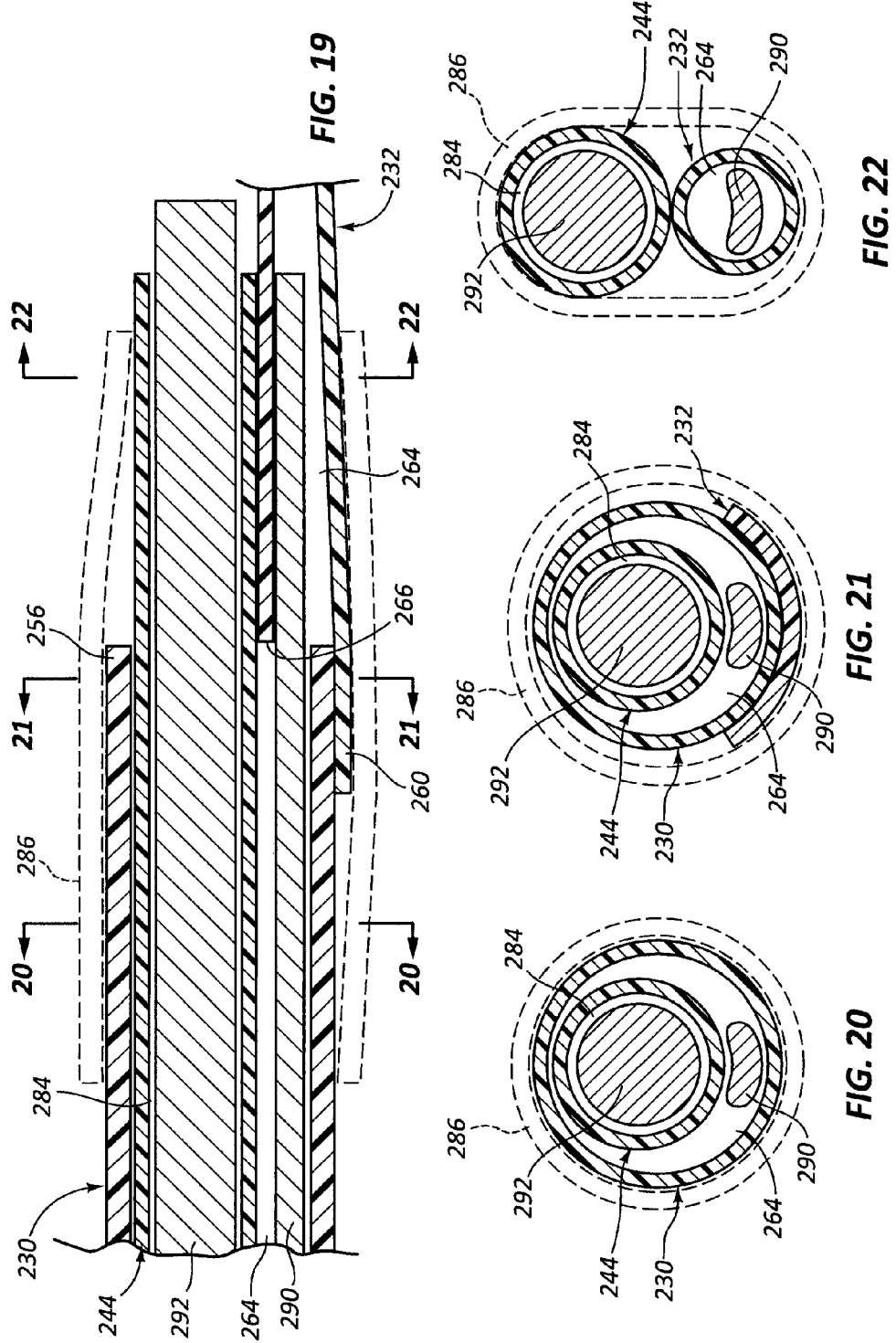

DUAL LUMEN BOND FOR VASCULAR CLOSURE DEVICE AND METHODS

CROSS-REFERENCE TO RELATED APPLICATION

This application claims the benefit of the filing date of U.S. Provisional Application No. 61/466,867, filed 23 Mar. 2011, and entitled DUAL LUMEN BOND FOR VASCULAR CLOSURE DEVICE AND METHODS, the disclosure of which is incorporated, in its entirety, by this reference.

TECHNICAL FIELD

The present disclosure relates to closure devices, and more specifically relates to lumen constructions for closure devices.

BACKGROUND

Various surgical procedures are routinely carried out intravascularly or intraluminally. For example, in the treatment of vascular disease, such as arteriosclerosis, it is a common practice to access the vessel and insert an instrument (e.g., a balloon or other type of catheter) to carry out a procedure within the vessel. Such procedures usually involve the percutaneous puncture of the vessel so that an insertion sheath can be placed in the vessel and thereafter instruments (e.g., catheters) can pass through the sheath and to an operative position within the vessel. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices.

A procedure for closing a puncture may require a plurality of operational steps that are performed by several vascular closure devices. One objective in such a procedure is to limit the number of devices inserted into the patient. Integrating functionality of several vascular closure devices into a single device poses a number of challenges.

SUMMARY

One aspect of the present disclosure relates to a vascular closure device that includes an inflation tube, a flashback tube, a dual lumen tube, a bond portion, and an inflatable balloon. The inflation tube defines an inflation lumen. The flashback tube defines a flashback lumen. The dual lumen tube has first and second lumens and is positioned distal of the inflation tube and flashback tube. The inflation tube and flashback tube are integrally connected to the dual lumen tube at the bond portion. The inflation lumen is in fluid communication with the first lumen. The flashback lumen is in fluid communication with the second lumen. The inflatable balloon is mounted at a distal end of the dual lumen tube and is in fluid communication with the inflation lumen.

The second lumen may terminate proximal of the inflatable balloon. The second lumen may be configured as a bioadhesive ejection lumen, wherein a bioadhesive is ejected through the second lumen. The system may also include a pull wire tube that defines a pull wire lumen. The pull wire tube extends through the first lumen and is connected to the dual lumen tube, the inflation tube, and the flashback tube at the bond portion. The system may include a sealing member positioned distal of the inflatable balloon, and a pull wire extending through the pull wire lumen. The sealing member may be detachably mounted to a distal end of the pull wire, wherein the pull wire is operable to release the sealing member. The distal sealing member may include a bioresorbable material. The pull wire tube may include a metal tube having a Teflon jacket.

Another aspect of the present disclosure relates to a method of making a vascular closure device. The method includes providing a vascular closure device having an inflation tube defining an inflation lumen, a flashback tube defining a flashback lumen, a dual lumen tube having first and second lumens, and an inflatable balloon. The method also includes bonding a distal end of the inflation tube and a distal end of the flashback tube to a proximal end of the dual lumen tube to provide fluid communication between the inflation lumen and the first lumen, and fluid communication between the flashback lumen and the second lumen, mounting the inflatable balloon to a distal end of the dual lumen tube and in fluid communication with the inflation lumen, and positioning a distal opening into the flashback lumen at a location proximal of the inflatable balloon.

Bonding the inflation tube and flashback tube to the dual lumen tube may include applying heat to form a bond portion that is an integral single piece construction. The second lumen may include a crescent shaped cross-section. The vascular closure device may include a wire tube defining a wire lumen, wherein the wire tube extends through the first lumen, and bonding including bonding the wire tube to the dual lumen tube, the inflation tube, and the flashback tube. The method may include removing a portion of a circumference of the inflation tube at a distal end of the inflation tube and inserting a portion of the dual lumen tube into the inflation lumen before bonding. The method may also include removing a portion of a circumference of the flashback tube at a distal end of the flashback tube and inserting a portion of the dual lumen tube into the inflation lumen before bonding. The dual lumen tube, the inflation tube, and the flashback tube may each comprise a polymer material, and bonding may include flowing the polymer material of the dual lumen tube, inflation tube, and flashback tube together as a unitary bond.

Another aspect of the present disclosure relates to a method of manufacturing a vascular closure device. The method includes connecting together a dual lumen tube, an inflation tube, and an sealing ejection tube at a joint positioned at a proximal end of the dual lumen tube, providing fluid communication between a first lumen of the dual lumen tube and an inflation lumen of the inflation tube, and providing fluid communication between a second lumen of the dual lumen tube and a sealing ejection lumen of the sealing ejection tube.

The method may also include mounting an inflatable balloon at a distal end of the dual lumen tube, wherein the inflatable balloon is in fluid communication with the first lumen and the inflation lumen. The method may include mounting a detachable sealing member distal of the inflatable balloon. Connecting together a dual lumen tube, an inflation tube, and an sealing ejection tube may include inserting a portion of the dual lumen tube into each of the inflation tube and the sealing ejection tube. Connecting together a dual lumen tube, an inflation tube, and an sealing ejection tube may include removing a portion of a distal end of the inflation tube and a distal end of the sealing ejection tube. Connecting together a dual lumen tube, an inflation tube, and an sealing ejection tube may include applying heat to the dual lumen tube, the inflation tube, and the sealing ejection tube to create an integral bond.

The foregoing and other features, utilities, and advantages of the invention will be apparent from the following detailed description of the invention with reference to the accompanying drawings.

BRIEF DESCRIPTION OF THE DRAWINGS

FIG. 2 is a side view of a closure device of the vascular closure system of FIG. 1.

FIG. 3 is a cross-sectional view of the closure device of FIG. 2 taken along cross-section indicators 3-3.

FIG. 4 is a cross-sectional view of the closure device of FIG. 2 taken along cross-section indicators 4-4.

FIG. 5 is a cross-sectional view of the closure device of FIG. 2 taken along cross-section indicators 5-5.

FIG. 7 is a cross-sectional view of the assembly of components shown in FIG. 6 assembled prior to bonding.

FIG. 8 is a cross-sectional view of the assembly of components shown in FIG. 7 taken along cross-section indicators 8-8.

FIG. 9 is a cross-sectional view of the assembly of components of FIG. 7 taken along cross-section indicators 9-9.

FIG. 10 is a cross-sectional view of the assembly of components of FIG. 7 taken along cross-section indicators 10-10.

FIG. 13 is a cross-sectional view of the components of FIG. 12 assembled prior to bonding.

FIG. 14 is a cross-sectional view of the assembly of components of FIG. 13 taken along cross-section indicators 14-14.

FIG. 15 is a cross-sectional view of the assembly of components of FIG. 13 taken along cross-section indicators 15-15.

FIG. 16 is a cross-sectional view of the assembly of components of FIG. 13 taken along cross-section indicators 16-16.

FIG. 19 is a cross-sectional view of the components of FIG. 18 assembled together prior to bonding.

FIG. 20 is a cross-sectional view of the assembly of components of FIG. 19 taken along cross-section indicators 20-20.

FIG. 21 is a cross-sectional view of the assembly of components of FIG. 19 taken along cross-section indicators 21-21.

FIG. 22 is a cross-sectional view of the assembly of components of FIG. 19 taken along cross-section indicators 22-22.

DETAILED DESCRIPTION

Figure 1:
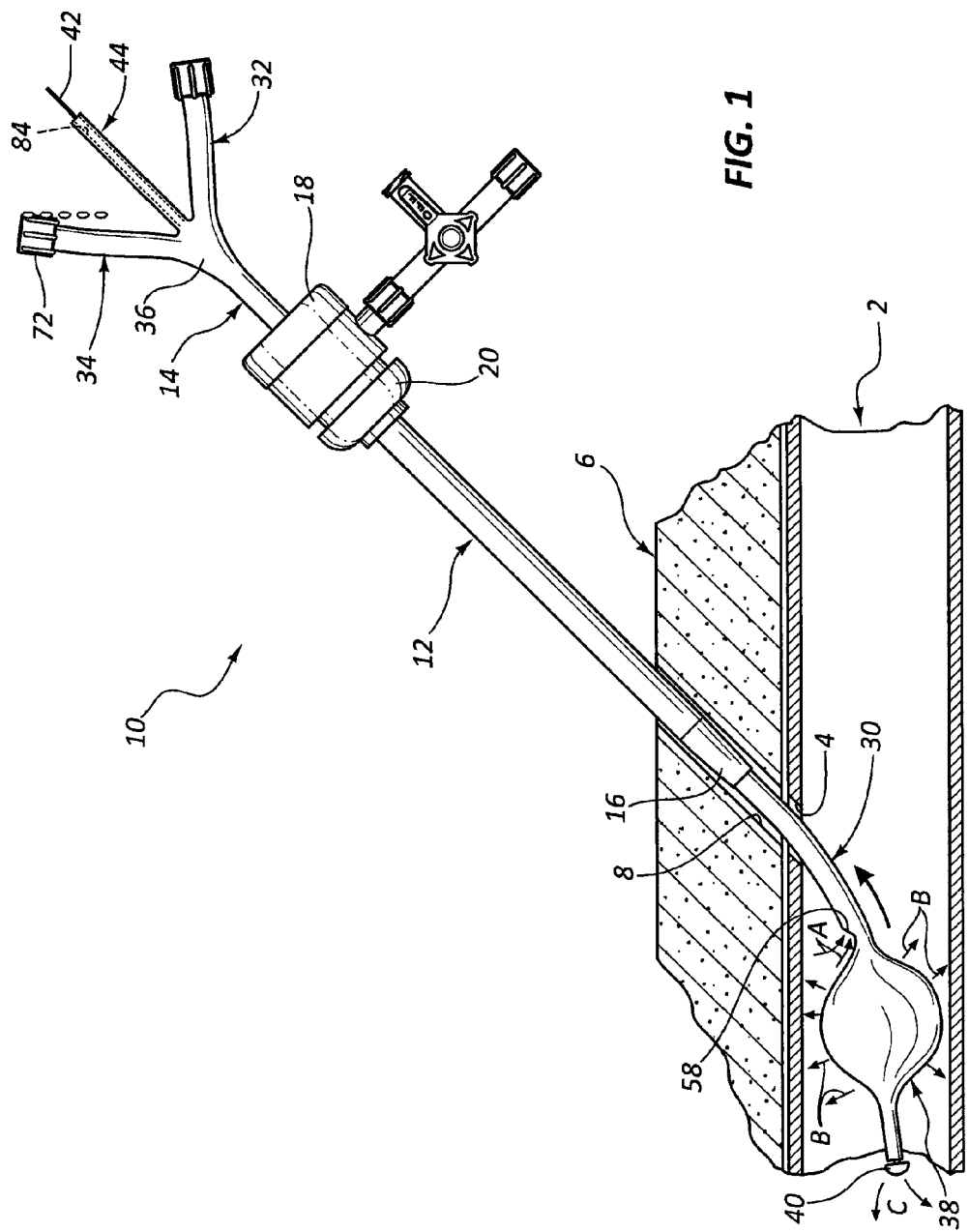
FIG. 1 is a side view showing a vascular closure system in accordance with the present disclosure inserted percutaneously into a vessel.

The present disclosure is directed to systems, devices and methods for closing a puncture in a tissue layer. An example application is a vascular closure system used to close a vessel puncture. The vascular closure system may include a closure device used to temporarily seal closed the vessel puncture while delivering a sealant to the puncture site. The sealant may be deposited on an exterior surface of the vessel adjacent to the vessel puncture to provide hemostasis upon removal of the closure device.

The closure device may include, for example, a blood flashback lumen that delivers a blood flow from a distal end portion of the closure device to a proximal end of the closure device. The closure device may include an expandable anchor such as, for example, an inflatable balloon that provides temporary sealing of the vessel puncture from within the vessel. The closure device may include multiple lumens that operate as, for example, a blood flashback lumen, inflation fluid lumen, and a sealant delivery lumen.

The closure device may also include a detachable sealing member that is configured to be deposited within or adjacent to the sealant upon removal of the closure device from the vessel. The detachable sealing member may be releasably mounted to the closure device with an attachment wire or other device that extends from a distal end of the closure device to a proximal end of the closure device at a location that is accessible for actuation by the operator. The attachment wire may extend through any one of the lumens defined along the length of the closure device.

The closure device may include multiple lumens consolidated within a single, relatively low-profile tubular construction for easy insertion of a distal end of the closure device through an insertion sheath and into the vessel. The lumens may be independently accessible at a proximal end of the closure device. The present disclosure provides a proximal bond region for the closure device wherein the lumens of the closure device are separated into separate tubes that can be manipulated independently of each other. In one example, the proximal bond region provides separation of a flashback lumen, inflation lumen, and wire tube, wherein the wire tube houses the attachment wire and the wire tube is positioned within the inflation lumen distal of the proximal bond region. The proximal bond region may be formed by application of, for example, heat or adhesives that create a fluid-tight seal and provide separation between the various lumens as the lumens transition into independent tubes.

The present disclosure also relates to methods of manufacturing a closure device and methods of sealing a tissue puncture. Example methods of manufacturing may include preparing tubing that is to be bonded together, inserting mandrels into the tubing, and bonding the tube ends together. Preparing the tubing may include forming a cut out in an end of the tubing (e.g., skiving an end of the tubing). Methods of closing a tissue puncture may include using a closure device with a proximal bond region to perform steps of, for example, providing blood flashback, inflating a balloon, delivering a sealant to the tissue puncture, and depositing a detachable sealing member via various lumens of the closure device accessible through the proximal bond region.

Referring now to FIG. 1, an example vascular closure system 10 includes a sheath 12 and a closure device 14. The sheath 12 and closure device 14 are configured to be at least partially inserted through a vessel puncture 4 of a vessel 2 and a percutaneous incision 8 of a tissue layer 6. Typically, the sheath 12 is first inserted into the percutaneous incision 8. The closure device 14 is then delivered through the sheath 12 and into the vessel 2. A closure device 14 may be used to seal closed the vessel puncture 4 extravascularly. Many other types of closure devices having different features and functionality from the closure device 14 may be used to seal closed the vessel puncture 4 and may benefit from the proximal bond features disclosed herein.

Referring to FIG. 1, the sheath 12 includes distal and proximal ends 16, 18, and a hub 20. The distal end 16 is insertable into a percutaneous incision 8 and/or vessel puncture 4. The closure device 14 is configured to be inserted into the sheath 12 at the proximal end 18.

The closure device 14 includes a dual lumen tube 30, an inflation tube 32, a flashback tube 34, a proximal bond portion 36, an inflatable balloon 38, a detachable sealing member 40, an attachment wire 42, and a wire tube 44 (see FIGS. 2-6). The inflation tube 32, flashback tube 34 and wire tube 44 are consolidated at the proximal bond portion 36 into the dual lumen tube 30. The dual lumen tube 30 typically has a smaller profile than if the inflation tube 32, flashback tube 34 and wire tube 44 were arranged side-by-side. Consolidating multiple tubes into the single dual lumen tube 30 may provide easier insertion and control of the lumens when operating the closure device 14.

The dual lumen tube 30 includes a first or inflation lumen 50, a second or flashback lumen 52, and distal and proximal ends 54, 56. The inflation lumen 50 may be in fluid communication with the inflation tube 32 at the proximal end 56, and be in fluid communication with the inflatable balloon 38 at the distal end 54. The flashback lumen 52 may be in fluid communication with the flashback tube 34 at the proximal end 56, and may be open at a distal inlet 58 near the distal end 54. The distal inlet 58 may be positioned proximal of the inflatable balloon 38. The attachment wire 42 is positioned in a wire lumen 84 (see FIG. 11) of the wire tube 44. The wire tube 44 may extend within the inflation lumen 50 from the distal end 54 to the proximal end 56.

The inflation tube 32 includes distal and proximal ends 60, 62, and an inflation lumen 64. During the manufacturing process, the inflation tube 32 may be skived or cut out at the distal end 60 (see FIG. 6). The inflation lumen 64 may be arranged in fluid communication with the second or flashback lumen 52. The proximal bond portion 36 may provide a transition between the inflation lumen 50 and the inflation lumen 64.

Figure 6:
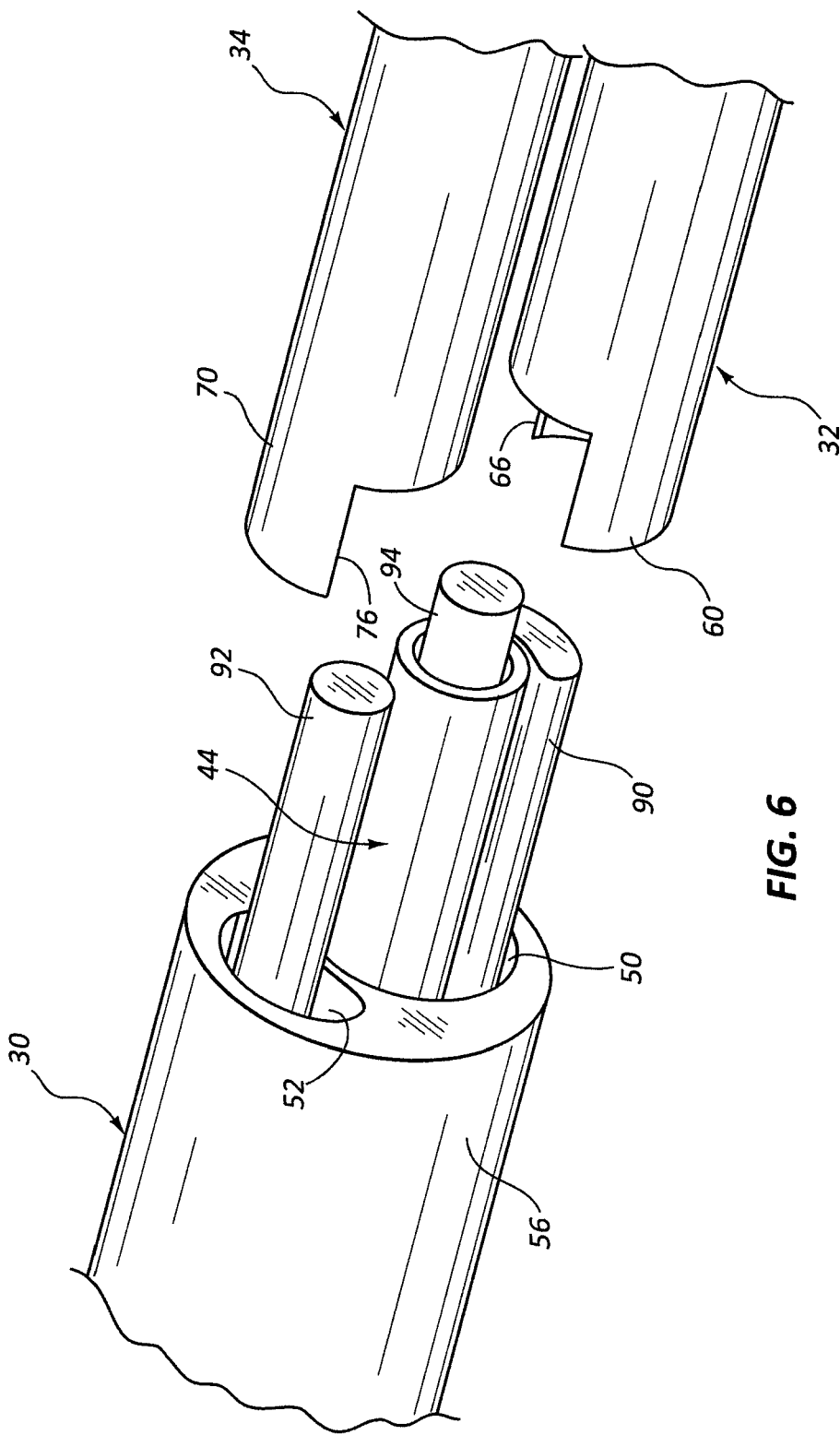
FIG. 6 is an exploded perspective view of components of the closure device of FIG. 2.

The flashback tube 34 may include distal and proximal ends 70, 72 and a flashback lumen 74. The distal end 70 may be skived or cut out as shown in FIG. 6 as part of the manufacturing process. The flashback lumen 74 may be arranged in fluid communication with the second or flashback lumen 52. The proximal bond portion may provide a transition between the flashback lumen 52 and flashback lumen 74.

The inflation tube 32 and flashback tube 34 may each include a hub or other connection member at their proximal ends 62, 72, respectively, for connection to, for example, a fluid source. The inflation tube 32 may be connected to a source of inflation fluid that is used to expand the inflatable balloon 38 in the direction B (see FIG. 1). Removing the inflation fluid from the inflatable balloon 38 contracts the inflatable balloon 38 into a collapsed or restricted position (see FIG. 2).

The proximal end 72 of the flashback tube 34 may be used as an outlet for a flashback blood flow that enters at the distal inlet 58 of the flashback lumen 52 (see FIG. 1). In some embodiments, the flashback lumens 52, 74 may be used to deliver a sealant to the vessel puncture 4 as part of a method of sealing closed the vessel puncture 4. A supply of sealant may be injected into the proximal end 72 of the flashback tube 34 and be delivered through the flashback lumens 52, 74 to the distal inlet 58 where the sealant is deposited within the percutaneous incision 8 adjacent to the vessel puncture 4. The inflated balloon 38 prevents the sealant from entering the vessel 2.

In operation, blood flow may enter the distal inlet 58 in the direction A (see FIG. 1), the inflatable balloon is inflated in the direction B (see FIG. 1), and the closure device 14 is withdrawn to provide a temporary seal between the inflated inflatable balloon 38 and the internal surface of the vessel 2 adjacent to the vessel puncture 4. After flashback blood flow ceases at the proximal end 72 of the flashback tube 34, the operator may aspirate the flashback lumens 52, 74 (e.g., apply suction to clear out contents from lumens 52, 74) and then deliver a supply of sealant through the flashback lumens 52, 74 and distal inlet 58 into the percutaneous incision 8. The sealant may be permitted to at least partially cure or set up into a solid or semi-solid state. The closure device 14 is withdrawn through the sealant and out of the patient. The sheath 12 may be removed from the percutaneous incision 8 prior to, during, or following removal of the closure device 14.

In some examples, a sealant tract is defined within the at least partially cured sealant after removal of the closure device 14. Some types of sealants may continue to expand or flow into the sealant tract to provide hemostasis. In other examples, the sealant tract may be plugged by detaching the detachable sealing member 40 within the sealant tract. The detachable sealing member 40 may be disconnected in the direction C (see FIG. 1) prior to removing the closure device 14. Typically, the detachable sealing member 40 is deposited outside of the vessel 2 and within the sealant at a location adjacent to the vessel puncture 4. The detachable sealing member 40 and sealant may comprise a bioadhesive or bioresorbable material.

Referring now to FIG. 6, components of the closure device 14 used to form the proximal bond portion 36 are shown in an exploded perspective view. The wire tube 44 is positioned within the inflation lumen 50. A first mandrel 90 is positioned within the inflation lumen 50 adjacent to the wire tube 44. A second mandrel 92 is positioned within the flashback lumen 52. A third mandrel 94 is positioned within the wire tube 44. The inflation tube 32 has a cutout 66 at the distal end 60. The flashback tube 34 has a cutout 76 at the distal end 70. The first mandrel 90 is inserted into the inflation lumen 50 and the distal end 60 extends around a portion of an outer surface of the dual lumen tube 30 at the proximal end 56. The second mandrel 92 is inserted into the flashback lumen 52 and the distal end 70 is inserted over a portion of the dual lumen tube 30 at the proximal end 56.

FIG. 7 illustrates the components of FIG. 6 assembled together and in a cross-sectional view. FIGS. 8-10 illustrate the arrangement of components shown in FIGS. 6 and 7 at various locations along the length of the assembly.

At least a portion of the assembly of components may be covered by a bond cover 86. The bond cover 86 may include, for example, a sleeve, heat shrink wrap, or other material that assists in bonding the components or holding the components together during bonding. In some arrangements, there is no overlap of the inflation tube 32 or flashback tube 34 with the dual lumen tube 30. The bond cover 86 or other structure (e.g., a beading or connecting material) may overlap an interface between the dual lumen tube 30 and inflation and flashback tubes 32, 34 to assist in creating a bond therebetween.

The first, second and third mandrels 90, 92, 94 may help maintain a continuous internal lumen structure during a bonding process. In one example, heat is applied to the assembly shown in FIG. 7 that causes the material of the dual lumen tube 30, inflation tube 32, and flashback tube 34 to flow together to create an integral single piece structure at the proximal bond portion 36. The heat may be applied using, for example, a hot jaw, laser, ultrasound, radio frequency (RF), or hot air torch.

In some arrangements, materials of the dual lumen tube 30, inflation tube 32, and flashback tube 34 comprise polymer materials that create an interlinking structure when bonded together. The mandrels 90, 92, 94 may comprise a metal material with a coating. The coating may help resist connection of materials of the tubes 30, 32, 34 to the mandrels 90, 92, 94 during the bonding process. Some example coatings for the mandrels 90, 92, 94 include Teflon® and related polymer materials.

The wire tube 44 may comprise a metal material and be formed as a hypotube. The wire tube 44 may comprise a polymer jacket comprising, for example, Teflon® and related polymer materials. The wire jacket may assist in bonding the wire tube 44 to materials of the dual lumen tube 30, inflation tube 32 and flashback tube 34 during the bonding process at the proximal bond portion 36.

The first, second and third mandrels 90, 92, 94 may have any shape and size. The first mandrel 90 is shown in FIGS. 6 and 8-10 having a crescent-shaped cross-section, while the second and third mandrels 92, 94 have a circular cross-sectional shape. The cross-sectional shape and size of the first, second and third mandrels 90, 92, 94 may match the pre-existing cross-sectional shape of the lumen within which they are fit prior to bonding. Alternatively, the cross-sectional shape and size of the mandrels may be used to change a shape or size of a lumen within which the mandrel is positioned as part of the bonding process in at least the proximal bond portion 36 of the closure device 14.

Figure 11:
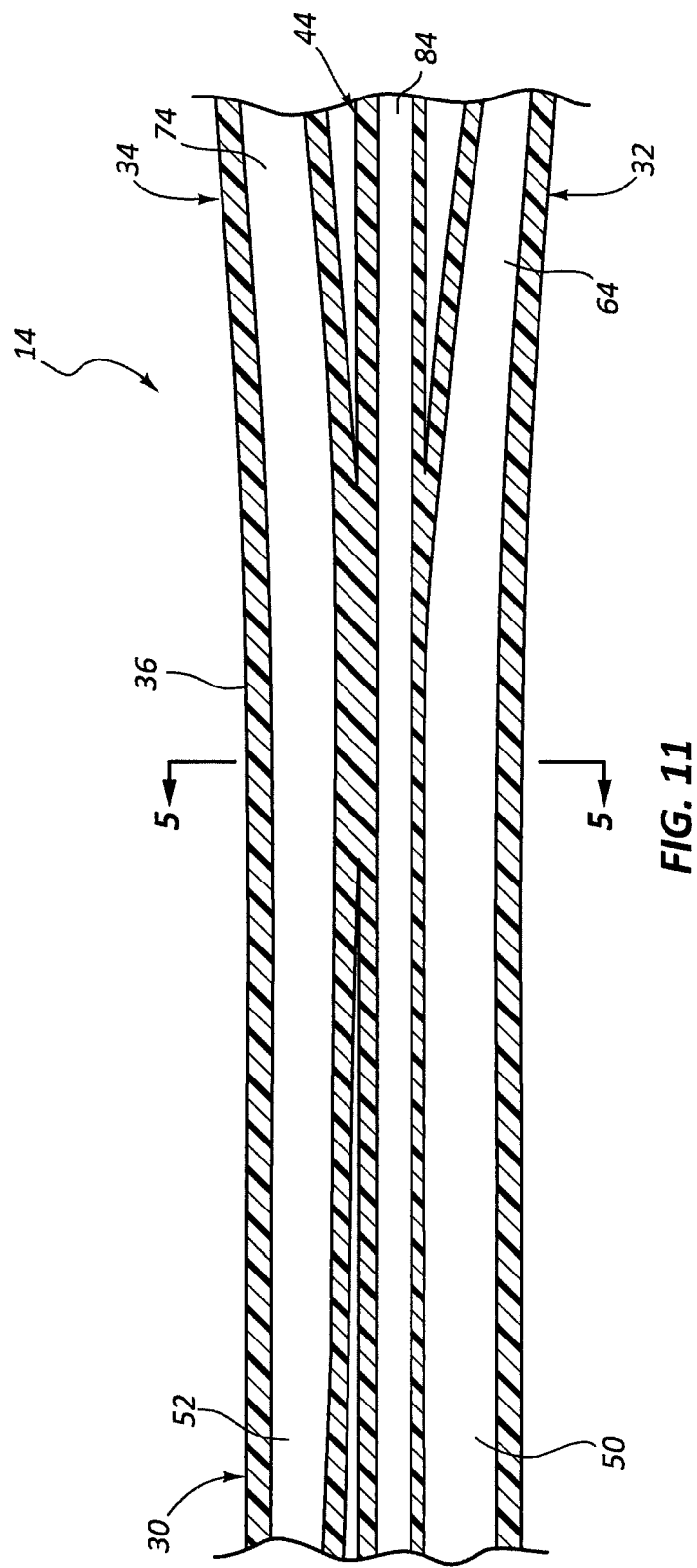
FIG. 11 is a cross-sectional view of the assembly of components of FIG. 7 after bonding.

FIG. 11 illustrates in cross-section the proximal bond portion 36 and portions of the closure device 14 located distally and proximally of the proximal bond portion 36. FIG. 5 shows a possible cross-sectional shape of the lumens defined in the closure device 14 at the proximal bond portion 36. FIG. 11 illustrates the integral, continuous material construction of the closure device 14 at the proximal bond portion 36. FIG. 11 also illustrates the dual lumen structure of the dual lumen tube 30 distal of the proximal bond portion 36, and the multitube arrangement of components proximal of the proximal bond portion 36.

One or more beading members 98 may be added to the assembly of components shown in FIG. 9 to assist in creating the proximal bond portion 36. The beading members 98 may be in the shape of spherical beads or have other shapes such as, for example, elongate, cylindrical shapes with any desired cross-sectional shape. The beading members 98 may comprise, for example, a polymer material which when heated increases a physical bond between at least some of the components of the assembly shown in FIG. 9.

Referring now to FIGS. 12-17, a portion of another example closure device 114 (see FIG. 17) is shown. The closure device 114 includes a dual lumen tube 130, an inflation tube 132, a flashback tube 134, and a proximal bond portion 136. The dual lumen tube 130 includes a first or inflation lumen 150, a second or flashback lumen 152, and a proximal end 156. The inflation tube 132 includes a distal end 160, an inflation lumen 164, and a cutout or skived portion 166. The flashback tube 134 includes a distal end 170, a flashback lumen 174, and a cutout or skived portion 176.

Figure 12:
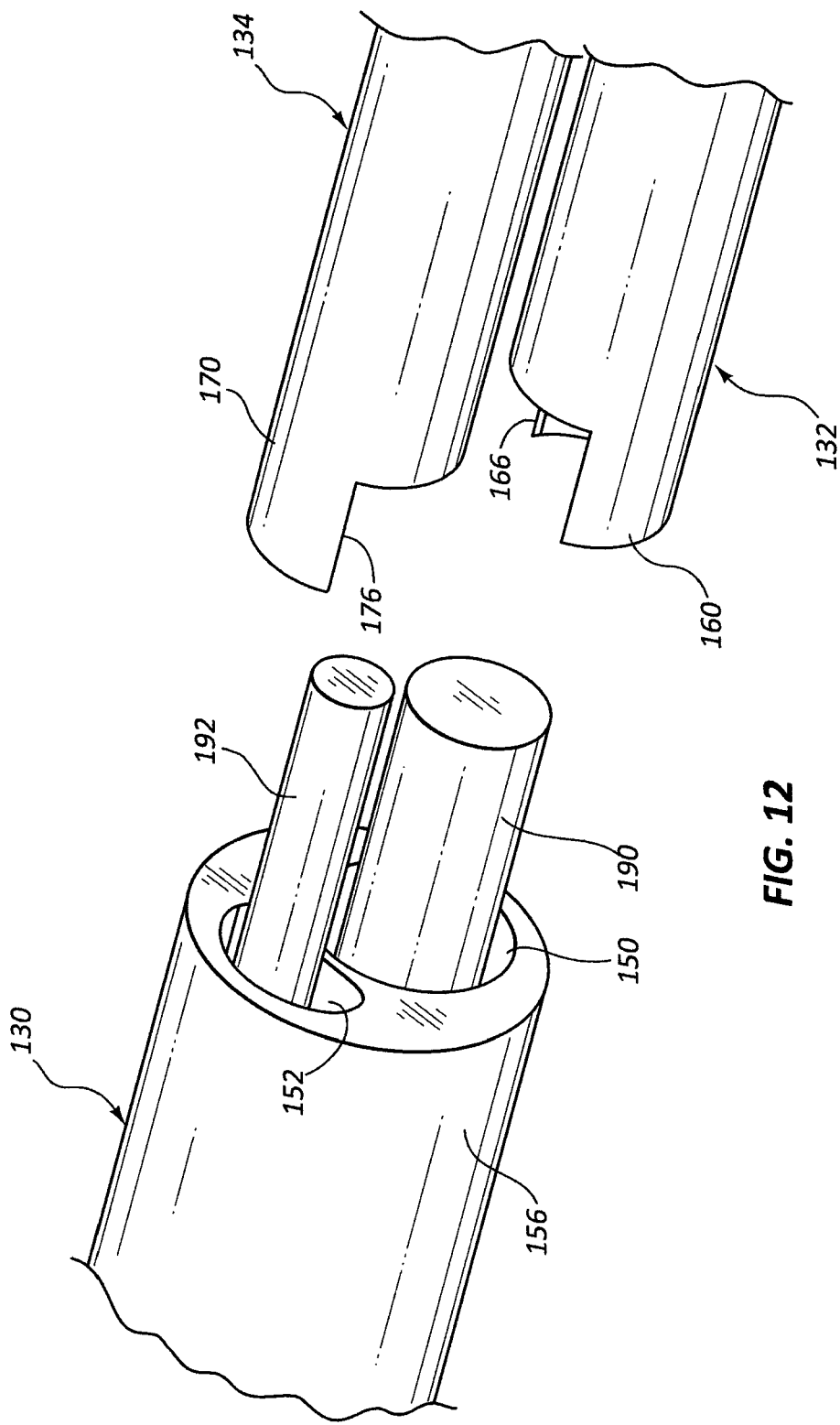
FIG. 12 is an exploded perspective view of components of another example closure device in accordance with the present disclosure.

Referring to FIG. 12, components of the closure device 114 are shown in an exploded perspective view prior to bonding. A first mandrel 190 is positioned in the inflation lumen 150. A second mandrel 192 is positioned in the flashback lumen 152. The inflation tube 132 includes a cutout 166 at the distal end 160. The flashback tube 134 includes a cutout 176 at the distal end 170. The first mandrel 190 is inserted into the inflation tube 132 and the distal end 160 of the inflation tube 132 is positioned overlapping the proximal end 156 of the dual lumen tube 130. The second mandrel 192 is inserted into the flashback tube 134 and the distal end of the flashback tube 134 is positioned overlapping the proximal end 156 of the dual lumen tube 130.

FIGS. 13-16 illustrate the components of FIG. 12 assembled together prior to bonding. FIGS. 14-16 are cross-sectional views showing the arrangement of mandrels and lumens at different locations along the length of the assembly of FIG. 13. At least a portion of the assembly shown in FIG. 13 may be overlapped with a bond cover 186. The bond cover 186 may have similar properties and functions as bond cover 86 described above.

Figure 17:
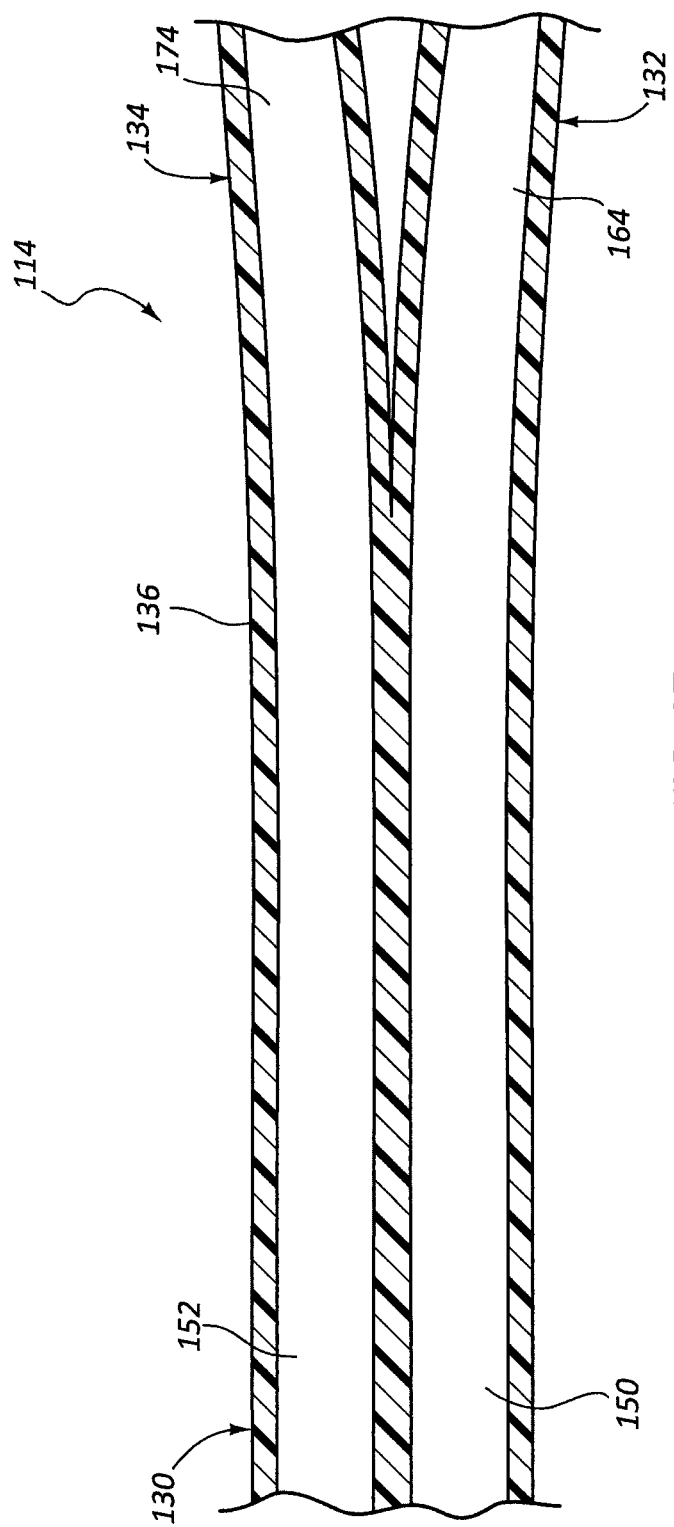
FIG. 17 is a cross-sectional view of the assembly of components of FIG. 13 after bonding.

The proximal bond portion 136 may be formed by bonding the dual lumen tube 130 to the inflation tube 132 and flashback tube 134. The proximal bond portion 136 may be formed by application of heat using, for example, a hot jaw, laser, ultrasound, radio frequency (RF), or hot air torch. In at least some arrangements, the proximal bond portion 136 includes an integral, continuous piece of material that transitions the dual lumen tube 130 to the inflation tube 132 and flashback tube 134, as shown in FIG. 17. In other arrangements, the proximal bond portion 136 comprises a plurality of fluid-tight seals that provide flow communication between the inflation lumens 150, 164 and flashback lumens 152, 174.

Figure 18:
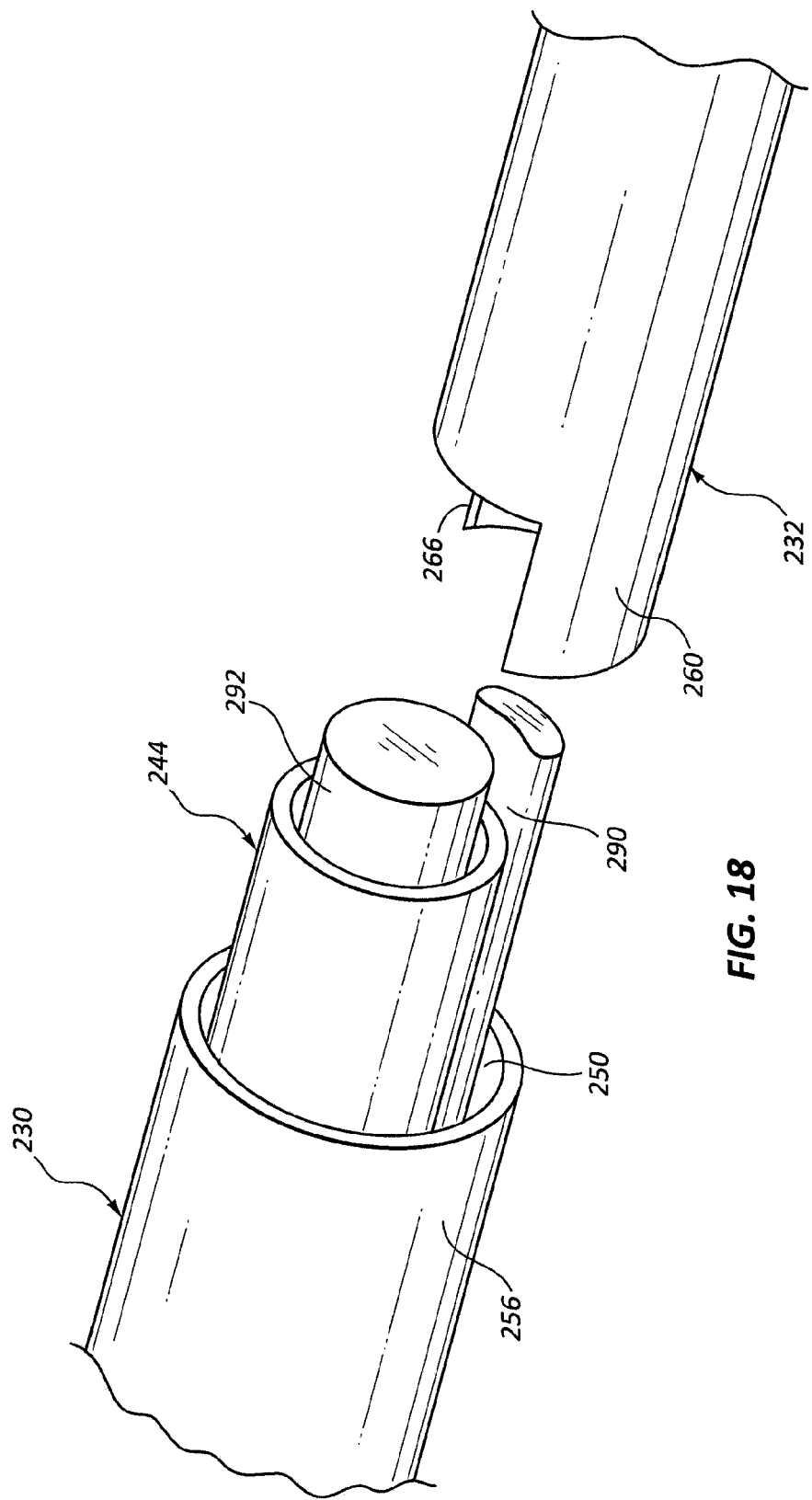
FIG. 18 is an exploded perspective view of components of another example closure device in accordance with the present disclosure.
Figure 23:
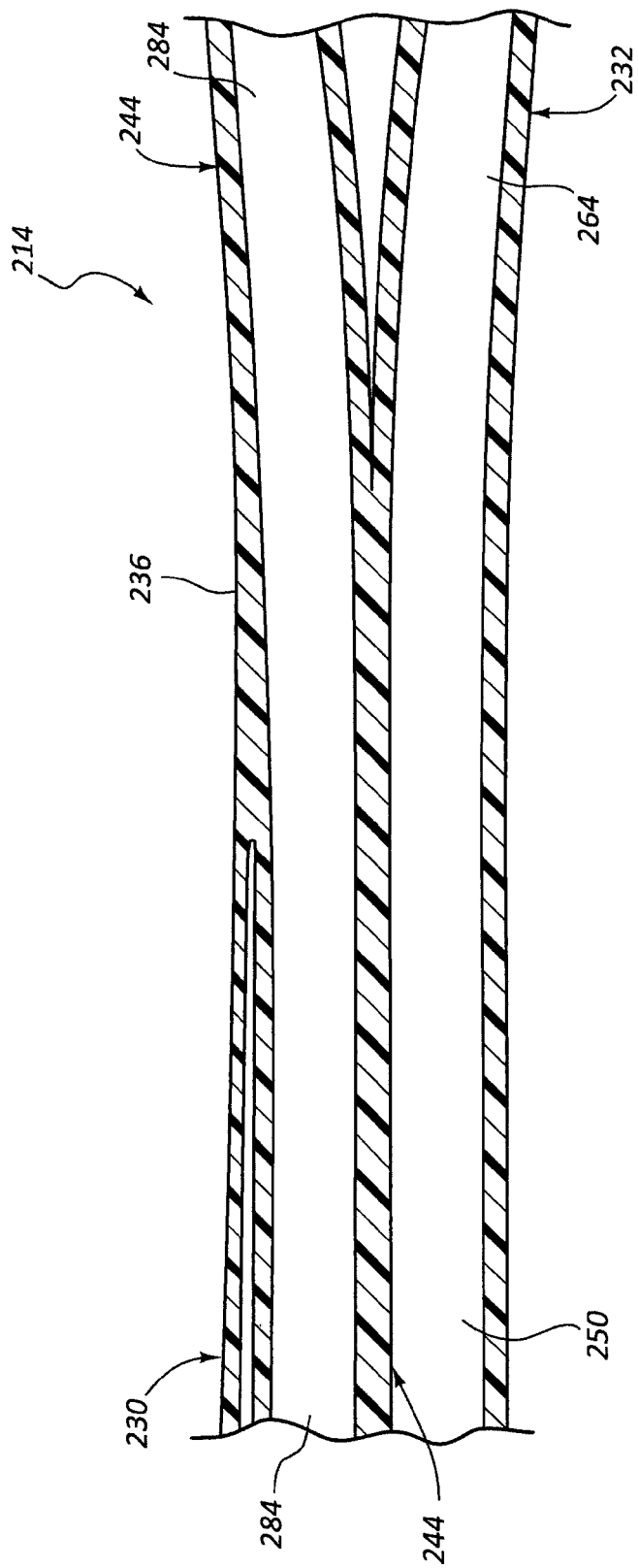
FIG. 23 is a cross-sectional view of the assembly of components of FIG. 19 after bonding.

Referring now to FIGS. 18-23, a portion of another example closure device 214 (see FIG. 23) is shown. FIG. 18 illustrates components of the closure device 214 in an exploded perspective view prior to bonding. The closure device 214 includes a lumen tube 230, an inflation tube 232, and a wire tube 244. The lumen tube 230 includes a first or inflation lumen 250 and a proximal end 256. The inflation tube 232 includes a distal end 260, an inflation lumen 264, and a cutout or skived portion 266 at the distal end 260. The wire tube 244 includes a wire lumen 284.

Prior to bonding, a first mandrel 290 is inserted into the inflation lumen 250, a second mandrel 292 is inserted into the wire tube 244, and the wire tube 244 is inserted into the inflation lumen 250. The inflation tube 232 includes a cutout or skived portion 266 at the distal end 260. The first mandrel 290 is inserted into the inflation lumen 264 with the distal end 260 overlapping a portion of the lumen tube 230 at the proximal end 256 (see FIG. 19). The first and second mandrels 290, 292 may have any desired size and cross-sectional shape. The wire tube 244 may comprise a polymer coating such as, for example, polytetrafluorethylene (PTFE) sold under the trademark Teflon® that improves bonding at a proximal bond portion 236.

A portion of the assembly of FIG. 19 may be at least partially surrounded or covered with a bond cover 286. The bond cover 286 may have the same or similar properties and function as the bond cover 86 described above.

FIGS. 20-22 illustrate cross-sectional views of the assembly of FIG. 19 at various locations along a length of the assembly prior to bonding. A proximal bond portion 236 may be formed to transition from a single-lumen lumen tube 230 with a wire tube 244 positioned therein, to side-by-side inflation tubes 232 and wire tube 244 (see FIG. 23). The proximal bond portion 236 may provide an integral, continuous material structure that transitions from the coaxial arrangement of lumen tube 230 and wire tube 244 distal of the proximal bond portion 236, to the side-by-side or radially spaced apart inflation tube 232 and wire tube 244 arrangement proximal of the proximal bond portion 236.

The closure device 214 shown in FIGS. 18-23 may have particular application where a flashback lumen is not needed or a flashback function is provided in a different way (e.g., a flashback lumen is positioned along an exterior surface of the lumen tube 230). In some arrangements, the wire tube 244 has other functions besides housing an attachment wire used to actuate a detachable sealing member. For example, the wire tube 244 may function as a flashback lumen that carries a flashback blood flow, an inflation lumen that is used to deliver and withdraw an inflation fluid, or a sealant delivery lumen used to deliver a sealant to a tissue puncture.

The lumen tube 230, inflation tube 232, and wire tube 244 may comprise any desired material construction. For example, the tubes 230, 232, 244 may comprise a metal hypotube with a polymer coating on the inside or outside surfaces thereof. In other examples, the tubes 230, 232, 244 may comprise multiple layers of polymer materials or a single polymer material.

The principles disclosed herein related to forming a proximal bond portion in a closure device may be applicable to other closure device constructions. The examples disclosed herein related to FIGS. 1-23 involve a dual lumen transitioning to two or three independent, side-by-side tubes, or a single lumen tube coaxially arranged with a second tube that transitions to a side-by-side tube arrangement. Other examples may include a three or more lumen tube that transitions to two or more independent, side-by-side arranged tubes, or a single lumen tube with multiple tubes positioned therein that transition to multiple independent, side-by-side arranged tubes. Many other constructions and arrangements are possible that could benefit from the principles described herein related to forming a proximal bond portion.

While this invention has been described with reference to certain specific embodiments and examples, it will be recognized by those skilled in the art that many variations are possible without departing from the scope and spirit of this invention. The invention, as defined by the claims, is intended to cover all changes and modifications of the invention which do not depart from the spirit of the invention. The words "including" and "having," as used in the specification, including the claims, shall have the same meaning as the word "comprising."

What is claimed is:

1. A vascular closure device, comprising:
    an inflation tube defining an inflation lumen;
    a flashback tube defining a flashback lumen;
    a dual lumen tube having first and second lumens that are fixed relative to each other, the dual lumen tube being positioned distal of the inflation tube and flashback tube;
    a bond portion wherein the inflation tube and flashback tube are integrally connected to the dual lumen tube with the inflation lumen in fluid communication with the first lumen, and the flashback lumen in fluid communication with the second lumen, the bond portion and dual lumen tube having an integral, single-piece construction;
    an inflatable balloon mounted at a distal end of the dual lumen tube and being in fluid communication with the inflation lumen.

2. A vascular closure device according to claim 1 wherein the second lumen terminates proximal of the inflatable balloon.

3. A vascular closure device according to claim 1 wherein the second lumen is configured as a bioadhesive ejection lumen, wherein a bioadhesive is ejected through the second lumen.

4. A vascular closure device according to claim 1 further comprising a pull wire tube that defines a pull wire lumen, the pull wire tube extending through the first lumen and being connected to the dual lumen tube, the inflation tube and the flashback tube at the bond portion.

5. A vascular closure device according to claim 4 wherein the pull wire tube includes a metal tube having a PTFE jacket.

6. A vascular closure device according to claim 4 further comprising a sealing member positioned distal of the inflatable balloon, and a pull wire extending through the pull wire lumen, the sealing member being detachably mounted to a distal end of the pull wire, the pull wire being operable to release the sealing member.

7. A vascular closure device according to claim 6 wherein the distal sealing member includes a bioresorbable material.

8. A vascular closure device, comprising:
    an inflation tube having an inflation lumen;
    a flashback tube having a blood flashback lumen;
    a dual lumen tube having first and second lumens that are fixed relative to each other, the dual lumen tube extending distally from the inflation tube and flashback tube;
    a pull wire tube extending through one of the first and second lumens;
    wherein the inflation tube, flashback tube, dual lumen tube, and pull wire tube are permanently connected together at a bond portion, the bond portion and dual lumen tube having an integral, single-piece construction.

9. The vascular closure device of claim 8, wherein the first lumen is in flow communication with one of the inflation lumen and the flash back lumen.

10. The vascular closure device of claim 8, wherein the pull wire tube extends side-by-side with the inflation tube and the flash back tube at a location proximal of the bond portion.

11. The vascular closure device of claim 8, wherein the bond portion has a continuous, integral construction comprising portions of the inflation tube, flashback tube, dual lumen tube, and pull wire tube.

12. The vascular closure device of claim 8, wherein the inflation tube, flashback tube, dual lumen tube and pull wire tube are heat bonded together at the bond portion.

13. The vascular closure device of claim 8, wherein the pull wire tube comprises a metal tube having a polymer jacket.

14. The vascular closure device of claim 8, further comprising an inflation balloon positioned at a distal end portion of the dual lumen tube and in flow communication with the inflation lumen.

15. A vascular closure device, comprising:
    a bond portion;
    an inflation tube extending proximally from the bond portion and having an inflation lumen;
    a flashback tube extending proximally from the bond portion and having a flashback lumen;
    a dual lumen tube extending distally from the bond portion and having first and second lumens in flow communication with the inflation lumen and the flashback lumen, respectively, the first and second lumens being fixed relative to each other;
    wherein the bond portion and dual lumen tube have an integral, single-piece construction.

16. The vascular closure device of claim 15, wherein the bond portion includes a connection between the inflation tube, flashback tube and dual lumen tube in an integral, single piece construction.

17. The vascular closure device of claim 15, wherein the second lumen terminates with a distal portion positioned proximal of the inflation balloon.

18. The vascular closure device of claim 15, further comprising a pull wire extending through the first lumen and the inflation lumen.

19. The vascular closure device of claim 15, further comprising a wire tube extending through one of the first and second lumens at a location distal of the bond portion.

20. The vascular closure device of claim 19, wherein the wire tube extends adjacent to the inflation tube and the flashback tube at a location proximal of the bond portion in a side-by-side arrangement.

21. The vascular closure device of claim 19, wherein the wire tube extends distally beyond the inflation balloon.

* * * * *